(12) United States Patent
Chauhan

(10) Patent No.: US 7,682,793 B2
(45) Date of Patent: Mar. 23, 2010

(54) IMMUNE COMPLEXES

(76) Inventor: Anil K. Chauhan, 1445 Ridgetree Trails Dr., Wildwood, MO (US) 63021

( * ) Notice: Subject to any disclaimer, the term of this patent is extended or adjusted under 35 U.S.C. 154(b) by 1387 days.

(21) Appl. No.: 10/485,326

(22) PCT Filed: Jul. 31, 2002

(86) PCT No.: PCT/US02/24301

§ 371 (c)(1),
(2), (4) Date: May 24, 2004

(87) PCT Pub. No.: WO03/012396

PCT Pub. Date: Feb. 13, 2003

(65) Prior Publication Data

US 2004/0219613 A1    Nov. 4, 2004

Related U.S. Application Data

(60) Provisional application No. 60/309,328, filed on Aug. 1, 2001.

(51) Int. Cl.
*G01N 33/53* (2006.01)
(52) U.S. Cl. ........................... 435/7.1; 436/518
(58) Field of Classification Search ................ 436/824, 436/507; 424/140.1; 530/412, 413, 415, 530/416, 868
See application file for complete search history.

(56) References Cited

U.S. PATENT DOCUMENTS

| | | | |
|---|---|---|---|
| 4,464,165 A | 8/1984 | Pollard, Jr. | |
| 4,512,763 A | 4/1985 | Schneider | |
| 4,551,435 A | 11/1985 | Liberti et al. | |
| 4,575,485 A * | 3/1986 | Sizto et al. | 435/7.9 |
| 4,627,915 A | 12/1986 | Kuroda et al. | |
| 4,664,913 A | 5/1987 | Mielke et al. | |
| 4,685,900 A | 8/1987 | Honard et al. | |
| 4,708,713 A | 11/1987 | Lentz | |
| 4,711,839 A * | 12/1987 | Singhal | 435/7.23 |
| 4,783,525 A | 11/1988 | McDonald | |
| 4,925,788 A | 5/1990 | Liberti | |
| 4,925,920 A | 5/1990 | Mannick et al. | |
| 4,945,039 A | 7/1990 | Suzuki et al. | |
| 5,017,471 A * | 5/1991 | Fellman | 435/5 |
| 5,037,649 A | 8/1991 | Balint, Jr. et al. | |
| 5,122,112 A * | 6/1992 | Jones | 604/6.04 |
| 5,211,850 A | 5/1993 | Shettigar et al. | |
| 5,215,908 A * | 6/1993 | Heinsohn et al. | 435/226 |
| 5,221,628 A | 6/1993 | Anderson et al. | |
| 5,223,441 A | 6/1993 | Ullman et al. | |
| 5,245,038 A | 9/1993 | Hale et al. | |
| 5,277,701 A | 1/1994 | Christie et al. | |
| 5,314,624 A | 5/1994 | Kawakura et al. | |
| 5,356,374 A | 10/1994 | Hogan et al. | |
| 5,484,396 A | 1/1996 | Naficy | |
| 5,510,466 A | 4/1996 | Krieger et al. | |
| 5,560,935 A * | 10/1996 | Konishi et al. | 424/520 |
| 5,593,897 A | 1/1997 | Potempa et al. | |
| 5,710,009 A | 1/1998 | Fitzpatrick et al. | |
| 5,733,254 A | 3/1998 | Jones et al. | |
| 5,782,792 A | 7/1998 | Jones et al. | |
| 5,783,087 A | 7/1998 | Vlock et al. | |
| 5,853,722 A | 12/1998 | Rollins et al. | |
| 5,855,616 A | 1/1999 | Fournier et al. | |
| 5,869,047 A | 2/1999 | Blake | |
| 6,030,614 A | 2/2000 | Muller-Derlich et al. | |
| 6,080,404 A | 6/2000 | Branham et al. | |
| 6,210,904 B1 | 4/2001 | Bednar et al. | |
| 6,218,521 B1 | 4/2001 | Obata | |
| 6,221,315 B1 | 4/2001 | Giesler et al. | |
| 6,245,752 B1 | 6/2001 | Barbera-Guillem et al. | |
| 6,251,394 B1 | 6/2001 | Nilsson et al. | |
| 6,261,571 B1 | 7/2001 | Hovanessian et al. | |
| 6,264,623 B1 | 7/2001 | Strahilevitz | |
| 6,355,669 B1 * | 3/2002 | Yamauchi et al. | 514/427 |
| 6,519,611 B1 | 2/2003 | Zong | |
| 6,600,014 B2 * | 7/2003 | Ogino et al. | 530/324 |
| 6,866,846 B1 * | 3/2005 | Heinrich et al. | 424/140.1 |
| 2001/0034028 A1 | 10/2001 | Link et al. | |
| 2002/0009771 A1 | 1/2002 | Hinuma et al. | |

FOREIGN PATENT DOCUMENTS

WO    WO 97/17980    5/1997

OTHER PUBLICATIONS

Wikipedia (online protein A definition).*
Amigorena et al., "FcγRII Expression in Resting and Activated B Lymphocytes," European J. Immunology, 1989, pp. 1379-1385, vol. 19.
Anderson et al., :"Phagocytosis Mediated by Three Distinct Fcγ Receptor Classes on Human Leukocytes," J. Experimental Med., 1990, pp. 1333-1345, vol. 171.

(Continued)

*Primary Examiner*—Jacob Cheu
(74) *Attorney, Agent, or Firm*—Sonnenschein, Nath and Rosenthal LLP

(57) ABSTRACT

A process for the preparation of active receptor and receptor complex fractions from cell lines expressing cell surface receptors which comprises applying ultrasonication to provide said expression to the cells in an aqueous (detergent free or substantially detergent free) composition.

17 Claims, 6 Drawing Sheets

OTHER PUBLICATIONS

Asanuma et al., "Clinical Hepatic Support By On-Line Plasma Treatment with Multiple Sorbents—Evaluation of System Performance," Trans. Am. Soc. Artif. Intern. Organs, 1980, pp. 400-405, vol. XXVI.

Bartok et al., "Comparison of the Binding of C3S and C3F to Complement Receptors Types 1, 2, and 3," J. of Immunology, 1995, pp. 5367-5375, vol. 154.

Caudwell et al., "Complement Alternative Pathway Activation and Control on Membranes of Human Lymphoid B Cell Lines," European J. Immunology, 1990, pp. 2643-2650, vol. 20.

Esposito-Farese et al., "Membrane and Soluble FcγRII/III Modulate the Antigen-Presenting Capacity of Murine Dendritic Epidermal Langerhans Cells for IgG-Complexed Antigens," J. Immunology, 1995, pp. 1725-1736, vol. 154.

Frade et al., "Analysis of gp140, a C3B-Binding Membrane Component Present on Raji Cells: A Comparison with Factor H," European J. Immunology, 1984, pp. 542-548, vol. 14.

Griffin et al., "Chapter 44—Plasmapheresis and Immunoadsorption," Maneuvers/Additional Interventions, pp. 597-611.

Kunkel et al., "Selective Removal of Circulating Immune Complexes from Patient Plasma," Artificial Organs, 2002, pp. 124-132, vol. 26.

Muta et al., "A 13-Amino-Acid Motif in the Cytoplasmic Domain of FcγRIIB Modulates B-Cell Receptor Signalling," Nature, 1994, pp. 70-73, vol. 368.

Peltz et al., "Cloned and Expressed Human Fc Receptor for IgG Mediates Anti-CD3-Dependent Lymphoproliferation," J. Immunology, 1988, pp. 1891-1896, vol. 141.

Pfueller et al.; "Successful Treatment of Patients with Systemic Lupus Erythematosus by Immunoadsorption with a C1q Column: A Pilot Study," Arthritis & Rheumatism, 2001, pp. 1962-1963, vol. 44.

Phillips et al., "Cross-Linking of B Lymphocyte Fcγ Receptors and Membrane Immunoglobulin Inhibits Anti-Immunoglobulin-Induced Blastogenesis," J. Immunology, 1984, pp. 627-632, vol. 132.

Ramos et al., "Complement-Dependent Cellular Cytotoxicity: Lumphoblastoid Lines That Activate Complement Component 3 (C3) and Express C3 Receptors Have Increased Sensitivity to Lymphocyte-Mediated Lysis in the Presence of Fresh Human Serum,"Proceedings of the National Academy of Sciences of USA, 1985, pp. 5470-5474, vol. 82.

Samuelsson, "Extracorporeal Immunoadsorption with Protein A: Technical Aspects and Clinical Results," J. Clinical Apheresis, 2001, pp. 49-52, vol. 16.

Sandor et al., "Lymphocyte Fc Receptors: The Special Case of T Cells," Immunology Today, 1992, p. 227-231, vol. 14.

Wiesenhutter et al., "Treatment of Patients with Refractory Rheumatoid Arthritis with Extracorporeal Protein A Immunoadsorption Columns: A Pilot Trial," J. Rheumatol., 1994, pp. 804-812, vol. 21.

Wernersson et al., "IgG-Mediated Enhancement of Antibody Responses is Low in Fc Receptor γ Chain-Deficient Mice and Increased in FcγRII-Deficient Mice," J. Immunology, 1999, pp. 618-622, vol. 163.

Suzuki, Kimihiro, et al., "Adsorption of Anti-Annexin V Using Dextran Sulfate Bound Cellulose Beads," Journal of Clinical Apheresis 15:262-265 (2000).

McLeod, Bruce C., "Introduction to the Third Special Issue: Clinical Applications of Therapeutic Apheresis," Journal of Clinical Apheresis 15:1-5 (2000).

Griffin et al, Plasmapheresis and Immunoadsorption. In: Austen KF, Burakoff SJ, Rosen FS, Strom, TB, Eds. Therapeutic Immunology, Second Edition: Chapter 44. Blackwell Sciences, Inc. 2001.

* cited by examiner

IMMUNE COMPLEXES

This application claims the benefit of priority of U.S. provisional application 60/309,328 filed Aug. 1, 2001, which is incorporated herein by reference in its entirety.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The present invention relates to development and use of active receptors and receptor complexes from naturally occurring, aberrant and genetically modified cell lines.

BACKGROUND OF THE INVENTION

Immune complexes (IC's) are formed in a person when an antibody binds to an antigen. Generally such immune complexes formed in small amounts in healthy persons are effectively removed by the person's mononuclear phagocytic system (MPS). However, in diseased persons, the immune complexes are formed in greater amounts and the diseased person's MPS is not able to effectively remove the IC's from the diseased person's plasma resulting in an overload in the person's system. As a result of an overload of these immune complexes in the person's circulation system, these immune complexes are deposited in the diseased person's tissue causing immunopathological reactions at various tissue sites.

The kind of immune complexes present in a person having a disease depend on the phase of the person's disease. There are two types of complexes.

In the initial phase of a disease, the amount of immune complex formed is excess antibody immune complexes and comprises antigen and antibody molecules. These types of complexes, apparently more insoluble, have a tendency to be deposited at various sites in the tissue. This type of IC's are also formed in situ at tissue sites and as noted above, cause immunopathological reactions.

During a late phase of disease, due to increased number of antigen molecules, a second type of immune complex comprising excess antigens and an antibody and a complement protein (a group of proteins present in the blood) is formed. These types of immune complexes are more soluble and circulate for a longer time in the blood. The immune complexes activate complement cascade, leads to formation of C5-C9 esterase activity that results in increased vascular permeability and release of vasoactive amines. It is desired to remove both types of IC's.

The removal of circulating immune complexes in Systemic Lupus Erythromatosus patients by C1q Immunoadsorption chromatography has provided beneficial effect to these patients.

BRIEF SUMMARY OF THE INVENTION

A process for the preparation of active receptor and receptor complex fractions from cell lines expressing cell surface receptors which comprises applying ultrasonication to provide said expression to the cells in an aqueous (detergent free or substantially detergent free) composition. The invention describes the development of processes to develop receptors and receptor complexes using ultrasonication or milder chelating agents. The active receptors or receptor complexes can be used in area of development of new soluble receptor based therapies, use as a solid phase in studying the interaction between receptors and ligands, use as a binding matrix in solid or soluble phase in high throughput screening during the drug development process.

In another aspect, the invention also comprises the active preparations of receptor complexes isolated from Raji cells and similar cells which shows specific binding to circulating immune complexes and their subsequent use in medical device to remove the complexes selectively from the patients plasma using extracorporeal systems. The invention also describes the further use of the immune complexes isolated by the use of the said technology.

In another aspect this invention comprises a process for the effective removal of immune complexes from plasma by adsorption of immune complexes to receptor attached to a solid support and the use of these complexes in identifying the disease associated proteins and modifications thereof.

DETAILED DESCRIPTION OF THE DRAWINGS

Figure 1:
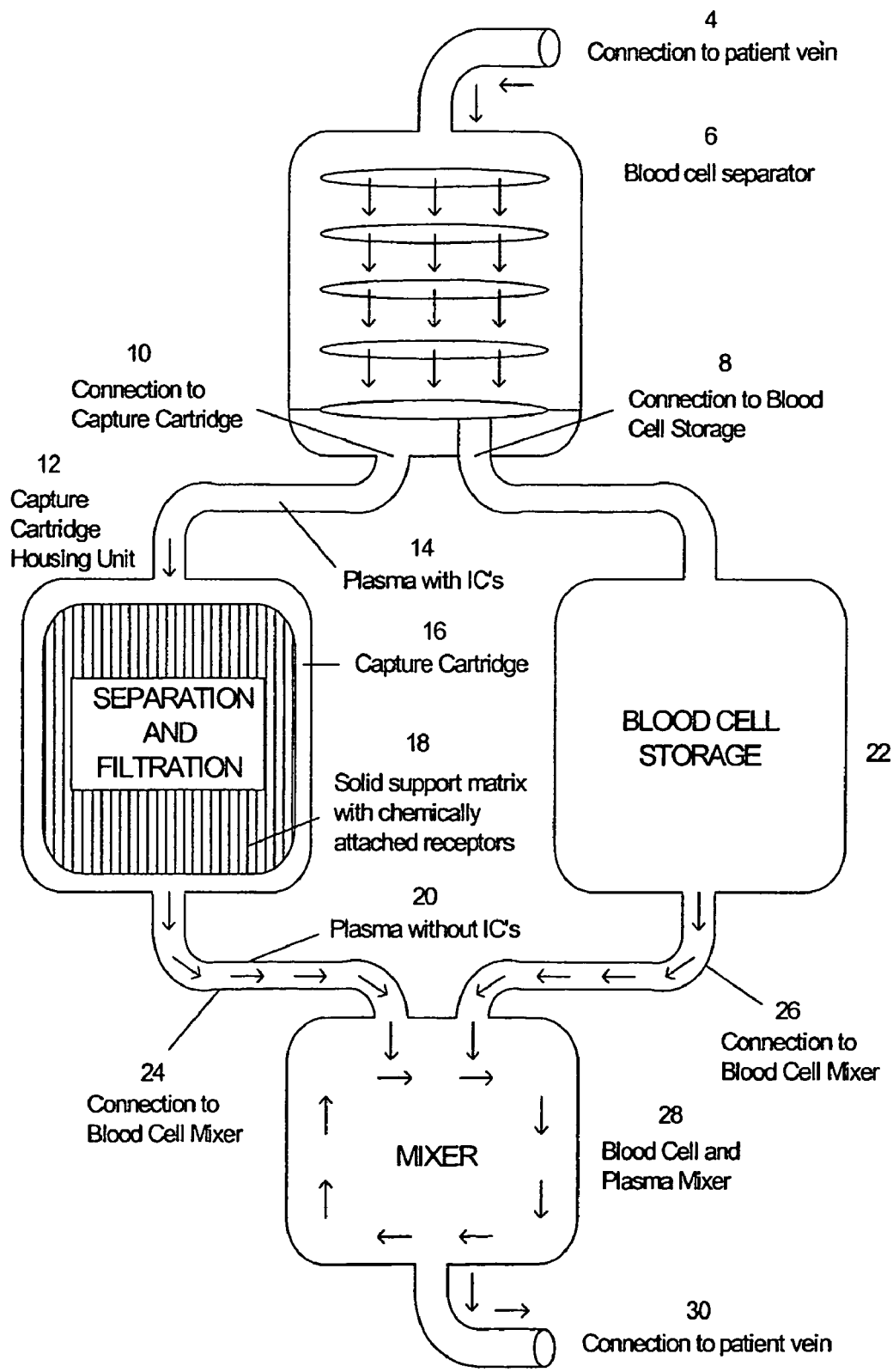
FIG. 1 is an exemplary embodiment of the invention showing separation of plasma and blood cells, and removal of immune complexes from plasma. (The direction of blood flow is shown by the arrows.)

Connections relating to FIG. 1 are shown as follows. More in detail with respect to FIG. 1, connection to patient vein (4) is a catheter (N/S) to vein of human patient (not shown). Surgically approved, pyrogen free tubing from vein catheter to blood cell separator (6). Blood cell separator (6). Connection to blood cell storage (8). Connection to capture cartridge (10) Capture cartridge housing unit (12), Plasma with IC's (14) Capture cartridge (16). Solid support matrix with chemically attached receptors (18). Plasma without IC's (20). Blood cell storage vessel (22). Connection to blood cell mixer (24). Connection to blood cell mixer (26) Blood cell and Plasma mixer (28). Connection from the blood cell mixer to patients vein catheter (30).

Figure 2:
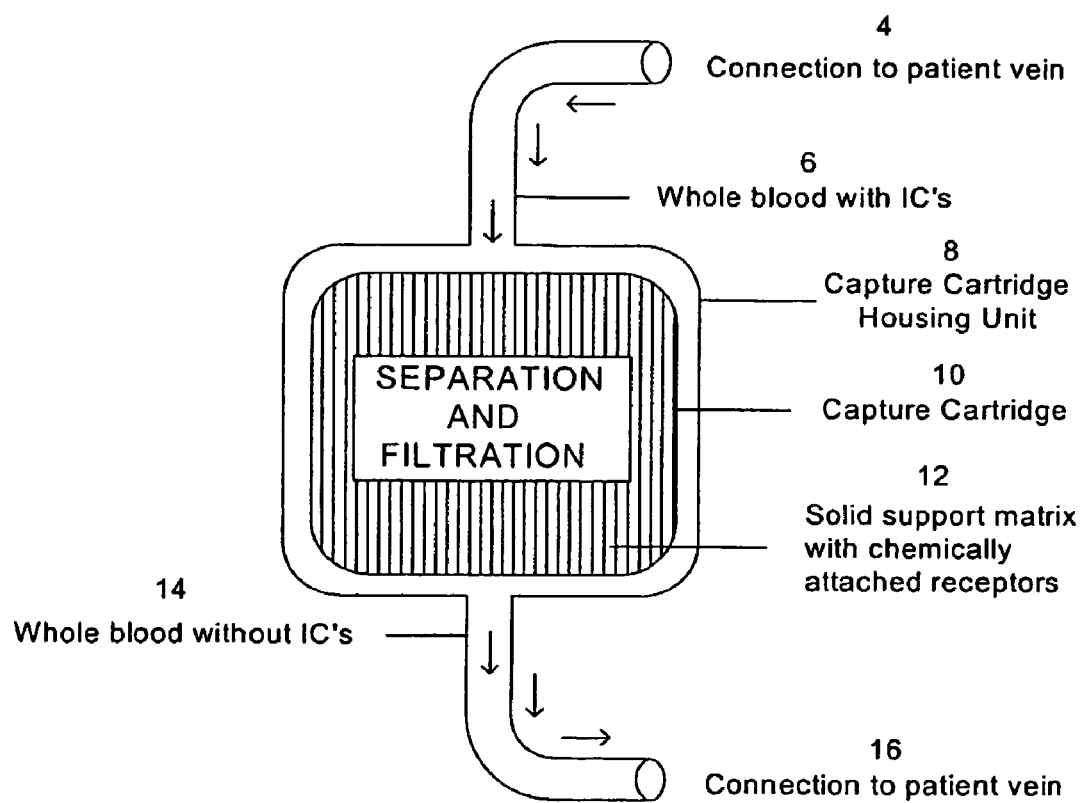
FIG. 2 is an exemplary embodiment showing a process with direct flow of blood over the solid support matrix with chemically attached receptors to remove immune complexes. (The direction of blood flow is shown by the arrows.)

Connections relating to FIG. 2 are shown as follows. (It is understood that the items are connected together as shown in FIG. 1 and FIG. 2.) More in detail with respect to FIG. 2, connection is a catheter to vein of human patient (not shown). Connection to patient vein (4). Whole blood with IC's (6) Capture cartridge-housing unit (8). Capture cartridge (10) Solid support matrix with chemically attached receptors (12). Whole blood without IC's (14) Connection to patient vein (16).

Figure 3:
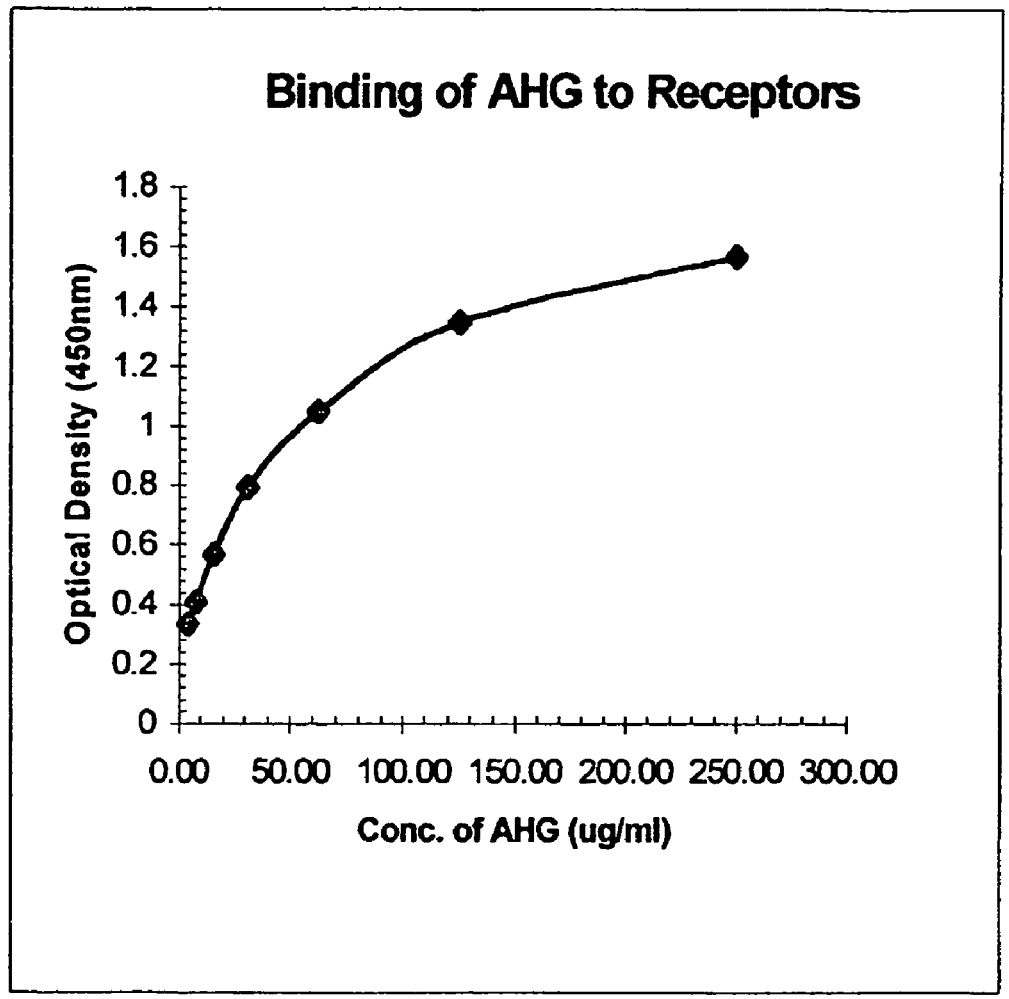
FIG. 3 is an exemplary embodiment showing binding of aggregated human Gammaglobulin to the receptor preparation. On the x-coordinate is the amount of AHG bound to receptors in microgram per milliliter. On the Y coordinate is the optical density at 450 nm.

FIG. 3 is an exemplary embodiment showing binding of aggregated human Gammaglobulin to the receptor preparation. On the x-coordinate is the amount of AHG bound to receptors in microgram per milliliter. On the Y coordinate is the optical density at 450 nm. The figure shows linear binding of the AHG to the receptors with increasing amount of protein concentration.

Figure 4:
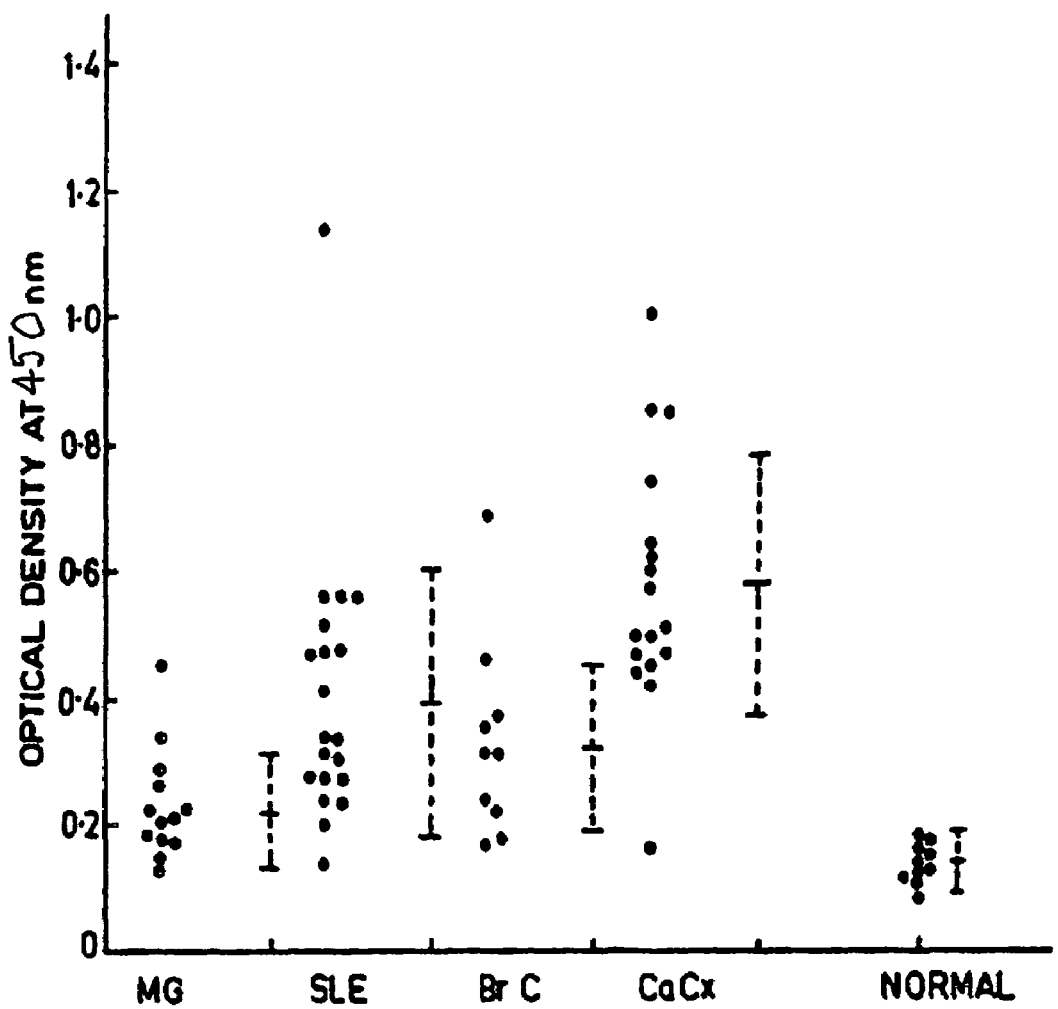
FIG. 4 is an exemplary embodiment showing levels of immune complexes in patients with disease: Myasthenia Gravis, Systemic Lupus Erythromatosus, Breast Cancer, Carcinoma cervix and normal human subjects. The X coordinate is the patient group, and the Y coordinate shows the comparative amount of immune complexes in the patient's plasma. The value is represented as the optical density measured at 450 nm (nanometers) (using ELISA reader).

FIG. 4 is an exemplary embodiment showing levels of immune complexes in patients with disease: Myasthenia Gravis, Systemic Lupus Erythromatosus, Breast Cancer, Carcinoma cervix and normal human subjects. The X coordinate is the patient group, and the Y coordinate shows the comparative amount of immune complexes in the patient's plasma. The value is represented as the optical density measured at 450 nm (nanometers) (using ELISA reader).

Figure 5:
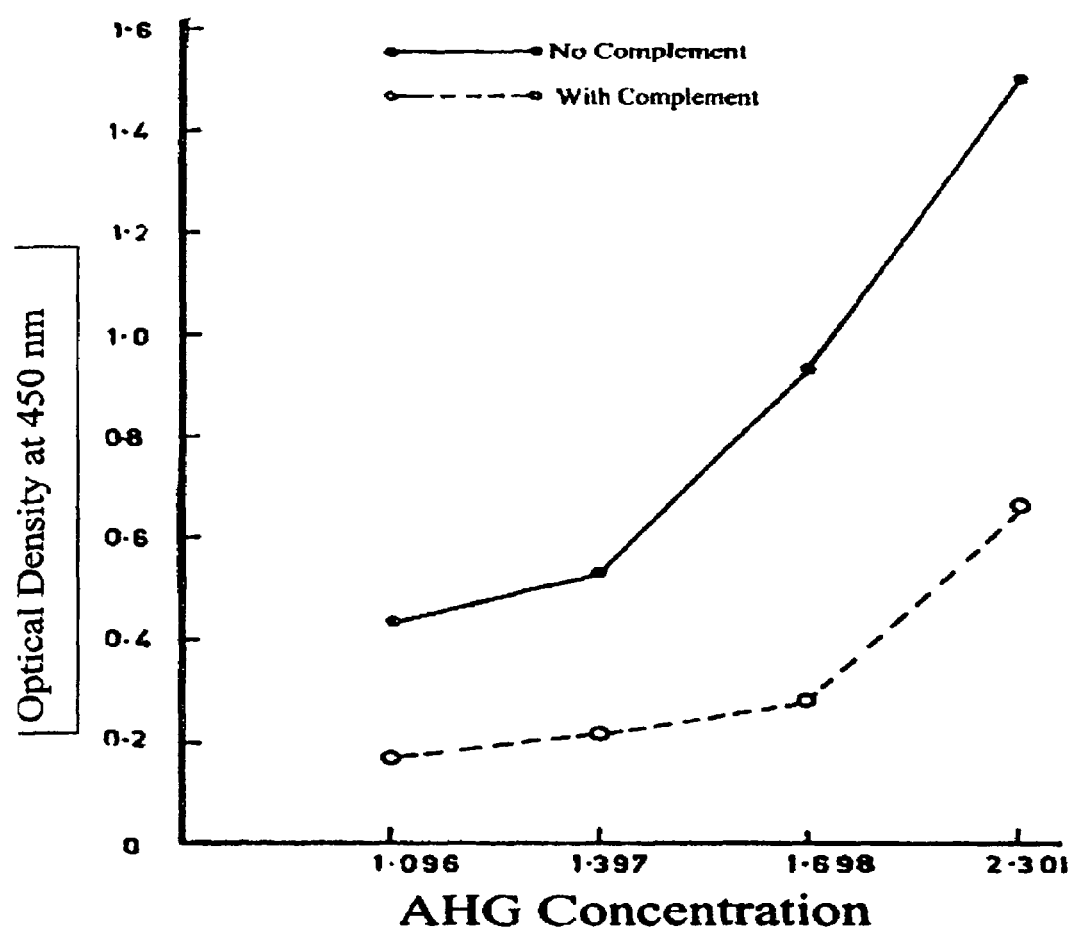
FIG. 5 shows effects of Guinea pig complement protein on the binding of aggregated human gamma globulin (AHG) to the receptor preparation. The X coordinate is the amount of AHG in microgram per milliliter, and the Y coordinate is the levels of AHG bound to receptor preparation. The value is represented as the optical density measured at 450 nm (nanometers) (using ELISA reader).

FIG. 5 shows effects of Guinea pig complement protein on the binding of aggregated human gamma globulin (AHG) to the receptor preparation. The X coordinate is the amount of AHG in microgram per milliliter, and the Y coordinate is the levels of AHG bound to receptor preparation. The value is represented as the optical density measured at 450 nm (nanometers) (using ELISA reader).

Figure 6:
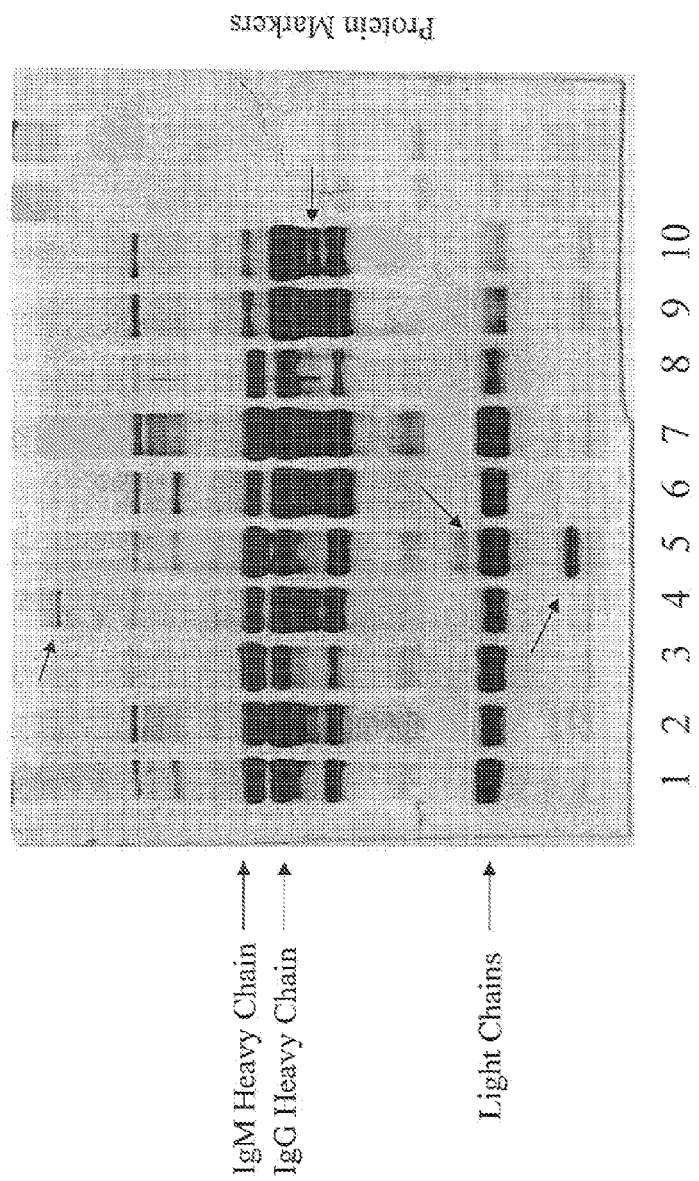
FIG. 6 shows protein profile of CIC bound to receptor preparation from juvenile rheumatoid arthritis and systemic lupus erythromatosus (human) displayed on SDS-PGAE.

FIG. 6 shows protein profile of CIC bound to receptor preparation from juvenile rheumatoid arthritis and systemic lupus erythromatosus (human) displayed on SDS-PAGE.

DETAILED DESCRIPTION OF THE INVENTION

The present invention provides a process for preparing active receptors and receptor complexes from naturally occurring, aberrant and genetically modified cell lines. In an embodiment, the invention comprises a process to prepare receptors and receptor complexes using ultrasonication or alternating one or more chelating agents. The active receptors or receptor complexes can be used in area of development of new soluble receptor based patient treatment therapies, use as a solid phase in studying the interaction between receptors and their specific ligand, use as a binding matrix in solid or soluble phase in high throughput screening during drug development process(es). In an embodiment, the invention comprises a process for the preparations of receptor complexes isolated from Raji cells which binds to circulating immune complexes. This invention has use as a medical device to remove the immune complexes selectively from the patient's plasma using extracorporeal systems. In this invention the receptor and receptor complexes bind to immune complexes. This binding is disrupted by contact or washing the bound receptor-immune complex with low pH buffer. The immune complex is released into the low pH buffer solution for removal and analysis. In this way the immune complexes are reduced or lowered in the plasma of the patient and released immune complexes are analyzed for disease associated or elevated proteins in the immune complexes.

A utility for this invention is the treatment of patients who have a need to have their immune complex(es) lowered or removed because of a disease state.

Biological signal and phenomena's are initiated in the natural systems by activation of receptors by their specific ligand. Most of the receptors are transmembrane glycoproteins. Even in enriched membrane fractions, they are minor species, co-inserted in the lipid bilayer with a c. $10^4$-fold excess, or greater, of other proteins. A critical step in the purification of these molecules is the dispersal of the bilayer, thus separating the various components so that they can be fractionated. The sonication of membranes, or their treatment with chelating agents (e.g. 1-10 mM EDTA, or EGTA), or high concentrations of salts (e.g. 1-2 Molar NaCl) or chaotropic agents (e.g. 10 mM lithium duiodosalicyclate), while valuable in extracting peripheral membrane proteins (i.e. proteins that are not inserted in the lipid bilayer and whose binding may be mediated by $Ca^{2+}$ or other ionic interaction) is insufficient to solubilize integral membrane proteins such as receptors. However, prolonged incubations of membrane fractions may, though endogenous proteolysis, lead to the liberation of water-soluble fragments of receptors, which in some cases may retain ligand-binding activity.

Using "Raji" a lymphoblastoid cell line of Burkit's lymphoma origin, the inventor has discovered that by applying ultrasonication to whole cells or treating whole cells with chelating agents, this invention can release active receptors or receptor complexes embedded in the lipid bilayer of the cells. As used herein, the term active include a functional receptor with binding activity to its ligand. The released receptor complexes still retain their binding activities as demonstrated by binding of the ligand and are active.

Receptors involved in immune system activation are B cell receptor (BCR), T cell receptor (TCR), Fc receptor (FcR) and Complement receptor (CR). The immune functions are elicited by interactions of immunoglobulin molecules to their receptors, complement molecules to complement receptors, cytokines to cytokine receptors and activations of T-cell receptor and B-cell receptor complexes. A number of molecules interacting with various classes and subclasses of immunoglobulin in different forms are described, which falls under the immunoglobulin superfamily. FcR exist for every antibody class: FcγR bind IgG, FcαR bind IgA, FcεR bind IgE, FcδR bind IgD and FcμR bind IgM. FcR receptors are members of immunoglobulin superfamily (IgSF); others belong to lectin families. Another class of receptors involved in immune mechanism is receptors to fragments of the complement proteins produced during activation of the complement pathway. Three opsonic fragments of C3 binds to four different receptors so named complement receptor Types 1 to 4 (CR1, CR2, CR3 and CR4). High affinity receptors of FcR i.e. FcR1, FcεR1, FcαR1, FcγR1 binds to monomeric immunoglobulin. Low affinity FcR do not bind to monomeric immunoglobulin with measurable affinity, they bind to aggregated immunoglobulin or antibodies complexed to multivalent antigens with a high avidity.

Hereinafter, there is described the preparation of the receptor complexes from the Raji cell's containing the low affinity FcR and complement receptors. Raji cells have shown to express the CR2 also referred as gp140 or C3 receptor (1-3), CR2, DAF and MCP molecules (4) cC1q-R, gC1q-R, (5) and FcγRIII (6). We also describe the use of these receptor complexes in the capture of circulating immune complexes.

Often receptors are present in clusters on the cell surface and for effecting their functions in many instances they cross-ligate with each other. The dimerization and receptor cross-linking is an established phenomenon in receptor biology. Antibodies and antigen-antibody complexes modulate the immune response. The precise molecular mechanism by which, these molecules up-regulate or down-regulate the immune response are largely unknown. Co-crosslinking the BCR with the CR-2 receptor complex (known to enhance B-cell activation in vitro), initiate efficient receptor mediated endocytosis by antigen presenting cells followed by presentation to T cells. Without being bound by theory, increased localization of immune complexes in lymphoid follicles on follicular dendritic cells (FDC) carrying complement receptor and Fc receptors (FcRs) may be an explanation for enhancement. Suppression of the antibody responses may result from elimination of complexes through receptor mediated phagocytosis, prevention of B cell recognition through epitope masking or via co-cross-linking of FcγRIIB and BCR, known to inhibit B-cell activation (7-10) as well as in vivo (11,12). It is essential for receptors in certain situations to be present in clusters as in our process to be effective to elicit their function. The presence of related receptors in vicinity of each other on the cell membranes allows them to dimerize, aggregate or cross-link to mediate their function.

Aggregation of multiple FcR may be essential to initiate signaling, aggregation of identical FcR is probably rare event. By contrast with antigen receptors, FcR are not clonally expressed, and most cells express more than one type of FcR. FcεRI, FcγRIIB, and FcγRIIIA are coexpressed by mast cells (13) and Langerhans cells (14); FcγRI, FcγRIIB and FcγRIIIA by murine macrophages; and FcγRI, FcγRIIA, and FcγRIIIB by human Neutrophils (15). When they interact with these cells, immune complexes of several isotypes are therefore likely to coaggregate more than one type of FcR. The coaggregation of different FcR on the same cell may have positive and negative effects. Lymphoid cells demonstrate the expressions of FcR with other receptors. FcγRIIB is expressed with BCR on B cells (16) and together with TCR on activated T cells (17). FcR those are coexpressed on a single cell functions as the subunits of multiple receptor complexes, which assemble when they are coaggregated by immune complexes. The qualitative and quantitative composition of such composite receptors is not predetermined. It depends on the cell type, on cytokines that differentially regulate the expression of various FcR, and on the composition of immune complexes with which they interact.

In this invention, the functional importance of presence and co expression of multiple receptors and their subsequent aggregation for the functional response is important.

In the present invention the inventors discovered a process to release the group of receptors from Burkits Lymphoma cell line "Raji" and a process to subsequently use them in capture of circulating immune complexes. The inventor prepares a fraction of soluble receptors and receptor complexes from Raji cells by ultrasonication and/or EDTA treatment of the Raji cells. Raji cells are an established cell line, which can be purchased from American Type Tissue Collection, 10801 University Blvd., Manassas, Va. 20110, U.S.A.

It is preferred that sonication be carried out in the absence of a detergent or surface active agent such that the cell line acqueous composition is substantially detergent free or is detergent free.

These soluble receptor protein complexes bind to both types of immune complexes. Raji cells have receptors to both complement (Complement Receptors also called CR) and to complexed form of antibodies (Fc receptors).

Thus receptor binding is carried out to the complexed form of antibody via Fc Receptors and binding to complement associated. with IC's to complement receptors.

The following are Fc Receptors for antibodies and Complement Receptors: Class I. Fc Receptors for antibodies, Fc alpha RI, Fc gamma RI, Fc gamma RIIa, Fc gamma RIIb1, Fc gamma RIIb2, Fc Epsilon R1, Fc Epsilon RII, Poly IgG receptor. Class II. Complement Receptors, CR1, CR2, CR3, CR4 and C1qR. In this invention, fraction of receptors binding specifically to IC are prepared from Raji cells.

The invention comprises a process for the preparation of active receptor and receptor complex fractions from cell lines expressing cell surface receptors which comprises applying ultrasonication effective to provide said expression to the cells in an aqueous detergent composition.

The concentration of cells in the composition ranges from about $0.1 \times 10^5$ cells/ml to about $10 \times 10^{10}$ cells/ml.

Preferably the concentration of cells is in the range from about $1 \times 10^6$ cells/ml to about $1 \times 10^8$ cells/ml.

Ultrasonication is used for a time sufficient to cause dispersion of the lipid bilayer of the cell membranes from a cell line expressing the receptor fraction.

The time ranges from about 2 minutes to 3 minutes in thirty second cycle and preferably the time ranges from about 0.5 minutes to about 7 minutes in 30 second cycle.

In an embodiment, the invention comprises a process for the preparation of active receptor and receptor complex fractions from cell lines expressing cell surface receptors, which comprises contacting cell lines with an effective concentration of chelating agents. Generally, the concentration of chelating agent is in the range from about 0.001% to about 1.5% by weight. Preferably, the concentration of chelating agent is in the range from a about 0.07% to about 0.125% by weight. Useful chelating agents include EDTA, EGTA, TED, GH, NTA and IDA. The cell line comprises a human cell line, which comprises cells selected from Raji, Daudi, RPMI 8866, Ramos and Clone 15 HL. The cell line comprises a mouse cell line. The mouse cell line includes 10P2, 10P12, 11 P0-1, My 43.51, BB88, D1B, T27A, D2N, BC16A, BC3A, RAW 264.7 and IC-21. In an embodiment, the cell line comprises a rat cell line. The rat cell line includes RBL-2H3 and RBL1. In an embodiment, the cell line comprises a canine cell line, which includes Dh82. Useful cell lines include those, which are genetically manipulated to introduce receptor genes. Preferably, the genetic manipulation involves introduction of gene coding for a receptor protein by process of transfection or electroporation.

Receptors Fc bind to the antibody of the first complex present in both tissue and blood. Complement receptors bind to the complement molecule, which is bound to the antibody of the second complex, which is in the blood.

Removal of immune complexes from blood and plasma is carried out in this invention.

In an embodiment, the invention comprises a process for the removal of immune complexes from a patient, said process comprising preparing active receptor and receptor complex fractions from cell lines expressing cell surface receptors and placing the receptor and receptor complex fractions on a suitable support and contacting said active receptor and receptor complex fractions with a patient's plasma containing immune complexes.

A useful support includes a cartridge preferably a filter or fiber, which is removable from a vent holding it. The cartridge preferably has pores in it.

The removed immune complexes are those, which are removable from plasma.

One type of patient is a human.

Useful active receptor and receptor complex fractions comprise cell proteins.

Useful human cell line's comprises: Raji, Ramos, Daudi and Clone 15 HL cells.

In an embodiment, the cell line comprises a mouse cell line.

Useful cell lines of a mouse cell line comprises 10P2, 10P12, 11 P0-1, My 43.51, BB88, D1B, T27A, D2N, BC16A, BC3A, RAW 264.7 and IC-21.

In an embodiment, the cell line comprises a rat cell line. Useful rat cells include RBL-2H3 and RBL1 cells.

A useful cell line comprises a canine cell line.

A useful cell line is a Dh82 cell.

In an embodiment, the genetic manipulation comprises introduction of gene coding for a receptor protein by a process of transfection or electroporation.

In an exemplary embodiment in FIG. 1, a connection is made to a patient's vein and blood is temporarily removed. Blood cell separation into plasma and blood cells follows. Separated plasma is routed to an adsorption unit and blood cells are routed to separate blood cell storage.

Separated plasma with the IC's is directed over fibers or membranes in a filtration unit. The IC's bind to receptors bound chemically to the fibers or membranes in the filtration unit.

Receptor bound IC's are retained on the fibers or the membranes of the filtration unit.

Plasma exiting the filtration unit is free of IC's and is combined with blood cells from blood cell storage in a mixer and then returned to the patient. In this embodiment, the patient receives his/her own blood and plasma back.

The illustrative solid support retaining the isolated IC's are now washed so that the IC's are removed, stored and analyzed for protein components.

Washing the solid support with physiological pH buffer and releasing immune complex(es) into the low pH buffer.

In an embodiment, one or more antigens are added onto the solid support in combination with receptors.

Useful antigen's comprises dsDNA, ANA, bacterial toxins and viral proteins.

In an embodiment, antibodies can be added onto the solid support in combination with receptors.

Useful antibodies include antibodies against dsDNA, ANA, bacterial toxins, and viral proteins.

If desired, the immune complexes may be analyzed by one of SDS-PAGE, high resolution two dimensional SDS-PAGE, HPLC, atomic mass spectroscopy and peptide mapping.

If desired, complement proteins are optionally added to the blood to be re-infused to the patient. These complement proteins bind with the first immune complex (antigen/antibody) deposited in tissue. This binding results in a complement binding to an antibody and antigen which is now sufficiently soluble so that the complement antibody/antigen complex moves from tissue to blood and is available for removal from blood by use of complement receptors, filtration etc.

The patient receives his/her blood back and is disconnected from this unit.

In an embodiment, the invention comprises a process of creating a database of useful protein information such as MPI (minimal protein identifier) for disease, associated proteins. The invention comprises of loading and storing analytical information relating to protein character and its relation to the disease, obtained from captured immune complexes associated with one or more specific diseases.

In an embodiment, the invention comprises a process wherein the immune complex comprises an antigen antibody complex from diseases including autoimmune disorders, renal disorders, neurological complications, hematological diseases, rheumatologic disease, infectitious diseases, organ transplants and neoplastic diseases.

Illustrative autoimmune disorders include Systemic Lupus Erythematosus, and Rheumatoid Arthritis.

Illustrative autoimmune disorders include Anti-Glomerular Basement Membrane Disease, Renal Vasculitis: Focal Necrotizing Glomerulonephritis (Rapidly progressive glomerulonephritis, Wegener's granulomatosus (WG), Microscopic polyangitis, Idiopathic RPGN), Focal Segmental Glomerulosclerosis, Anti-Glomerular Basement Membrane Disease.

Illustrative treatable neurological disorders include Myasthenia Gravis, Eaton-Lambert Syndrome, Guillain-Barre' syndrome, Amyotrophic Lateral Sclerosis, Inflammatory Polyneuropathy, and Multiple Sclerosis.

Illustrative treatable hematological disorders include Myeloma and Cryoglobulinemia, Thrombotic Thrombocytopenic Purpura, Idiopathic Thrombocytopenic Purpura, and Allaoantibodies in Hematologic Disease.

Illustrative disorders include Rheumatoid Arthritis, Rheumatoid Vasculitis, Scleroderma, Dermator, Early stages of scleroderma, Dermatomyositis, Polymyosistis, Sjogren's syndrome and Behcet's disease.

In an embodiment, a treatable disease is a viral infection or a bacterial infection.

An illustrative use of the invention is in organ transplant(s) including kidney transplants, bone marrow transplant and heart transplant.

A treatable neoplastic disease is a solid tumor.

In an embodiment, the invention comprises a process for preparing active receptor and receptor complex fractions from cell lines expressing cell surface receptors, which comprises applying ultrasonication to the cells in an aqueous (detergent-free) containing composition or alternately contacting the cells with an effective concentration of one or more chelating agents, (A) placing the receptors on a support,
(B) contacting receptors with at least one suitable ligand,
(C) obtaining initial data indicating whether the ligand has bound to at least one receptor.

Data taken includes at least one peptide map, protein sequence, SDS-PAGE, atomic mass spectra, high-resolution two dimensional gel, phosphorylation site, DNA binding sites, protein-protein interaction sites and receptor binding sites data.

The ultrasonication comprises applying sonication to the cell lines in an amount of time and at a frequency sufficient to prepare active cell receptor fractions.

In an embodiment, a solid support is employed. Useful solid supports include resin and fibers made from Polypropylene, Polyethersulfone, Polyvinylidene Fluoride, Polytetrafluoro-ethylene, Polystyrene, Cellulose, Activated charcoal on cellulose, Microza, Superdex, Superose, Sephacryl, Sephadex and Sephadex LH.

One embodiment of the present invention provides a process wherein the support comprises a cartridge housed in a container.

Another embodiment of the present invention provides a process wherein the cartridge comprises a filter or a hollow fiber cartridge.

Another embodiment of the present invention provides a process wherein the cartridge is a removable cartridge.

In yet another embodiment of the present invention, a process is provided wherein the cartridge has pores.

One embodiment of the present invention provides a process wherein the cartridge has pores with a range from about 0.2 milli-microns to about 200 milli-microns.

In another embodiment of the present invention, a process is provided wherein the cores have a size of about 0.45 milli-microns to about 45 milli-microns.

Another embodiment of the present invention provides a process wherein the cartridges number from one to about 100 and are removable from a cartridge containing vessel.

In an embodiment, the invention comprises a process further comprises contacting a receptor with at least one of a humanized monoclonal antibody, monoclonal antibody, other active molecules, peptides and mimotopes and obtaining data indicative of whether the binding of ligand to receptor has been inhibited.

In an embodiment, data indicative of binding of ligand to receptor is obtained in the presence with humanized monoclonal antibodies, monoclonal antibodies, other active molecules, peptides and mimotopes and in the absence of the said material is compared to data indicative of whether the said material has inhibited the binding of the ligand to receptor.

In an embodiment, the invention additionally comprises inoculating a patient with the immune complex in combination with immunity enhancing factors or in vitro treatment of cells with immune complexes captured form the patient and re-inoculating or injecting such cells after the treatment, wherein the immune complex alters the immune response in the patient.

The patient is a human patient in an embodiment.

In an embodiment, the immune complexes are used in association with at least one of an antigen, antibody and a chaperon.

The examples below are provided to illustrate the subject invention and are not included for the purpose of limiting the invention.

EXAMPLE

1. Preparation of Receptors and/or Receptor Complexes

Actively multiplying Raji cells 6HAT were harvested and washed three times with cold PBS. Cells were counted and adjusted to a concentration of $3.0 \times 10^7$ cells/ml. The suspension was sonicated with MSE sonicator (Fischer Scientific) at a maximum energy output for three minutes in six cycles of 30 seconds each. The sonicated suspension was centrifuged at 2000 rpm for 15 minutes at 4° C. The pellet was discharged and supernatant was centrifuged again at 105,000 g for 90 minutes (Sorvall OTD-50 centrifuge). The supernatant was aspirated, aliquoted and stored at −70° C. The pellet was suspended in cold PBS, aliquoted and stored at −70° C. Similarly K 562 a myeloid leukemia cell line used as control was treated similarly to Raji cells. The pellet and supernatant was stored at −70° C. till used.

2. Preparation of Aggregated Human Gama Globulin (AHG):

Cohn fraction II (Sigma Chemicals, St. Louis, USA) was dissolved in phosphate buffered saline (PBS) at a concentration of ten milligram per ml and incubated at 63° C. for half an hour. Following incubation the solution was centrifuged at 1500 g for 30 minutes. The pellet was discarded and supernatant was again subjected to centrifugation at 130,000 g for 90 minutes in ultracentrifuge (Beckman Coulter Inc., 4300 North Harbor Blvd. Fullerton<CA-92834). The pellet was re-suspended in PBS and homogenized in a glass homogenizer. The suspension was centrifuged at 10,000 g for half an hour, pellet was discarded and supernatant was aliquoted and stored at −70° C. Protein estimation of the receptor preparation and AHG, was carried out by Lowry's Method (Lowry et al., 1951).

3. Raji Cell Receptor ELISA for Estimation of Immune Complexes

Fifty micrograms of receptor preparation (supernatant fraction) was diluted in 10 ml of coating buffer (Sodium bicarbonate buffer, pH 9.6) and 100 µl of this solution was added to each well of 96 well micro ELISA plate (Flow Laboratories). The plate was covered and kept overnight at 4° C. under humid conditions. After discarding the solution, 100 µl of 0.25% BSA dissolved in PBS containing 0.05% Tween-20 was added to each well to block the remaining free sites on the plate. The plate was again incubated at 4° C. for two hours. After washing the plate thrice with PBS/Tween-20, 100 µl of different dilutions of AHG, or 1:20 dilution of serum to be tested was added to the wells, the plate was returned for incubation at 37° C. in humid chamber for three hours. Thereafter, the plate was washed thrice with PBS/Tween-20 solution and 100 µl anti-human IgG peroxidase conjugate was added to each well (previously titrated to give a value of OD 1.0 with 100 nano-gram of IgG). The plate was incubated for two hours at 37° C. The plate was again washed thrice with PBS/Tween-20. Thereafter, 100 µl of TMB substrate was added to each well Reaction was allowed to occur until the color developed and then terminated by addition of 50 µl of 2.5 M $H_2SO_4$. Optical density in each well was then recorded using a Dynatech ELISA-Reader at 450 nm. Optical density was plotted against the AHG concentrated to get a standard curve.

Illustration of the presence of Receptors for binding to Immune Complexes

Raji cells have been extensively used in the estimation of circulating immune complexes.

Example 1

Demonstration of presence of Fc receptors and binding of aggregated human gamma globulin and immune complexes In this example the binding of aggregated human gamma globulins (AHG) to the receptor fraction in phosphate buffered saline was demonstrated. Data is shown in the Table following. The linear binding pattern seen with the increasing concentration of AHG demonstrates that the AHG is binding to the receptor preparation via Fc receptors, as there is no other component, which could justify the binding of AHG to the preparation.

| | | AHG Concentration in µg/ml of protein | | | | | |
|---|---|---|---|---|---|---|---|
| | | 6.25 | 12.5 | 25 | 50 | 100 | 200 |
| Amount of | 12.5 | 0.6 | 0.6 | 0.7 | 0.9 | 1.3 | 2.0 |
| Protein in solid | 25 | 0.5 | 0.5 | 0.7 | 0.9 | 1.2 | 1.9 |
| phase in µg/ml | 50 | 0.5 | 0.6 | 0.7 | 0.9 | 1.4 | 2.1 |
| | 100 | 0.4 | 0.6 | 0.7 | 0.9 | 1.3 | 1.9 |

Demonstration of Two Binding Activities:

Example 2

Raji cell receptors (supernatant fraction) at a concentration of 25 ug/10 ml was coated in bicarbonate buffer in solid phase at 4° C. overnight. The plates were washed thrice with PBS/Tween 20. A serial dilution of AHG in PBS/Tween 20 was mixed with varying dilution of fresh guinea pig complement and allowed to react at 37° C. After half an hour 100 µof each dilution is added to the plate, simultaneously the same AHG dilution without complement was also added. The plate was incubated at 37° C. for three hours and remaining procedure was followed as described in earlier experiment.

Example 3

The receptor preparation was radiolabel led using Iodogen. The reaction was carried out by adding 0.5 mCi $I^{125}$ Sodium Iodide to 10 µl of receptor preparation. The reaction was allowed to proceed for ten minutes. To this mixture was added 50 μl of 0.25% BSA in phosphate buffer. The mixture was chromatographed over Ultrogel. Each fraction was counted to determine the presence of labeled protein.

From each of the fractions 6000 cpm were mixed with 100 μl of AHG (containing 5 μg). The tubes were allowed to stand at 37° C. for two hours. Afterward 100 μl of antihuman IgG was added to each tube. The tubes were allowed to stand at 4° C. overnight. The precipitated bound proteins and supernatant (free unbound activity) was separated and counted in the Gamma Spectrometer (LKB).

The peak fractions were checked for binding with 10 μl of AHG in PBS/Tween 20 with 5% NHS. A fixed number of counts 25000 cpm from two peaks fraction no. 3 and no. 8 were incubated at 37° C. for three hours with various concentration of AHG in presence of 5% NHS. The reaction mixture was then precipitated with antihuman IgG. It was observed that fraction no. 3 showed a uniform decline in the binding activity with increasing concentration of AHG, the maximum binding activity 48% at 1.6 μg/ml and minimum binding activity 19% at 251 g/ml. On the contrary the fraction no.8 showed increased binding with the increasing concentration of AHG. The binding being maximum (54%/0) at 25 g/ml and minimum (23%) at 1.6 μg/ml.

This example demonstrated the presence of two different activities in the preparation. We concluded that fraction three contained predominantly the complement receptors and fraction eight contained predominantly the Fc receptors. Knowing the molecular weight of the complement receptors being generally higher than that of Fc receptors, it was concluded that the fraction, which eluted earlier on ultrogel contained the complement receptors.

Example 4

Over one hundred samples from human patients with the following diseases 1.SLE 2.Rheumatoid Arthritis 3.Myasthenia Gravis 4.Breast cancer 5. Carcinoma Cervix. The levels of immune complexes present in these human patients were correlated with matched normal serum samples. A statically significant increase in the patients was demonstrated in the level of immune complexes between the two groups.

Example 5

The receptor preparation was coupled to NHS activated Sepharose FF 4B (Pharmacia). One to two ml of plasma from SLE and juvenile rheumatoid arthritis patients was applied to the column. The column was subsequently washed and the bound material was eluted with Glycine-HCl buffer. The material was analyzed on SDS-PAGE. The reported band at proper resolution was observed in the gel. The unique bands are marked with arrow.

The receptors can be attached to any of useful membranes, hollow fibers or any other fibers comprising: Polypropylene, Polyethersulfone, Polyvinylidene Fluoride, Polytetrafluoroethylene, Polystyrene, Cellulose, Activated charcoal on cellulose, and Microza.

Alternate support is also a chromatography support matrix, available from 1. Amersham Pharmacia Biotech (800, Centennial Avenue, Piscataway, N.J., 08854 2. Biorad Laboratories 3. Whatman 4. TosoHas (156 Keystone Drive Montgomeryville, Pa. 18936) 5. Millipore corporation (80, Ashby Road, Bedford, Mass. 01730-2271): Superdex, Superose, Sephacryl, Sepahdex, Sephadex LH.

The receptor preparation can be attached to any of the above material(s) with or without spacer arm by a suitable chemical reaction such as 1. NHS-Ester Reaction, 2. Imidoester reaction, 3. EDC Reaction 4. Maleimide Reaction, 5. Active halogen reaction 6. Pyridyl Disulfide Reaction or 7. Hydrazide Reaction.

Reagents needed for the above mentioned chemical reactions are available from 1. Pierce Chemical Company, 3747 N. Meridian Rd., PO Box 117, Rockford, Ill. 61105 2. Molecular Probes, 4894 Pitchford Avenue, Eugene, Oreg. 97402, USA.

Preferred Properties of Fibers and Membrane (solid support)
1. Inert;
2. Non-leach ability of construction material or bound material;
3. Chemical activation of the material to bind to ligand receptors.

Manufacturer of the Basic Materials for Useful Membranes and Hollow Fibers

Dupont
1007 Market Street
Wilmington, Del. 19898 USA
Asahi KaseiHibiya-Mitsui Building
1-2 Yurakucbo 1-chome, Chiyoda-ku
Tokyo 100-8440, JAPAN
Pall
2200 Northern Blvd.
East Hills, N.Y. 11548 USA
Millipore
80 Ashby Road
Bedford, Mass. 01730 USA
TosoHas
156 Keystone Drive
Montgomeryville, Pa. 18936 USA Immune complexes bound to receptors, which are attached chemically to solid phase, can be released using any low pH buffer such as Glycine-HCl, or chaotropic salts i.e. Guanidine hydrochloride.

Equipment useful for separation of blood cells and plasma is usually referred as 1. Celltrifuge 2. Continuous flow cell separator 3 Discontinuous flow cell separator.

Useful cell types herein include:
Raji Cells, Daudi Cells, RPMI 8866, Ramos.2G6.4C10 and Clone 15 HL-60 (Human cell line with Fc and Complement receptors)
BB88, D1B, T27A, BC16A, D2N, RAW264.7, IC21 and BC3A (Mouse cell lines with Complement receptors)
10P2, 10P12, 11PO-1, IC21, A20 [A-20] (Mouse cell lines with Fc receptors)
RBL-2H3 and RBL1 (Rat cell line with Fc receptors)
Dh82 (Dog cell line with Fc and Complement receptor)
J774 (macrophage-like cell line)
18.81 (pre-B cell line)
Derivative of any of the above cell lines or CHO cell lines or any other mammalian cell lines engineered genetically for expression of complement and/or Fc receptors. Genetically engineered receptors into a yeast or any other expression system.

Types of known receptors useful in the process of the invention herein include:
FcγR1A, FcγRIIA, FcγRIIB1, FcγRIIB2, FcγRIIC, FcγRIIIA, FcγRIIIB, FcγRn, FcαR1, FcαRII, FcεRI, FcεRII, FcδR, FcμR Illustrative antigens which are a component(s) at times of circulating immune complexes.

Rheumatoid Factor (Rh factor in Rheumatoid Arthritis), double stranded DNA (dsDNA in SLE), Nuclear Antigens (NA in SLE), 58 kD and 78 kD monocytic membrane proteins with affinity to acetylcholine receptor (Myasthenia Gravis).

Types of antibody isotypes captured in an embodiment herein: IgA, IgM, IgG1, IgG2a, IgG2b, IgG3, IgG4, IgE and IgD.

The type of diseases for which the device of this invention might be useful:

Renal Diseases
Anti-Glomerular Basement Membrane Disease
Renal Vasculitis: Focal Necrotizing Glomerulonephritis
  Rapidly progressive glomerulonephritis
  Wegener's granulomatosus (WG)
  Microscopic polyangitis
  Idiopathic RPGN
Focal Segmental Glomerulosclerosis
Systemic Lupus Erythematosus
Anti-Glomerular Basement Membrane Disease
Neurologic Disease
Eaton-Lambert Syndrome
Guillain-Barre' syndrome
Amyotrophic Lateral Sclerosis
Myasthenia Gravis
Inflammatory Polyneuropathy
Multiple Sclerosis
Hematologic Disease
Myeloma and Cryoglobulinemia
Thrombotic Thrombocytopenic Purpura
Idiopathic Thrombocytopenic Purpura
Allaoantibodies in Hematologic Disease
Rheumatologic Disease
Rheumatoid Arthritis
Rheumatoid Vasculitis
Scleroderma
Dermator
Early stages of scleroderma
Dermatomyosistis
Polymyosistis
Sjogren's syndrome
Behcet's disease
Dermatological Disease
Pemphigus Vulguris associated to antibodies to squamous epithelium
Bullous pemphigoid associated to antibodies to dermal basement membrane In an embodiment, an immune complex is isolated by elution from the membrane or fiber can be electrophoresed on sodium dodecyl sulfate polyacrylamide gel. The antigenic component from these complexes will be sequenced to identify the protein associated with the diseases. The association between the antigen and disease etiology will be established. A high-resolution two-dimensional SDS-PAGE gel map will be developed there from. The protein will be analyzed by MALDI-TOF atomic mass spectroscopy.

While the invention has been described in terms of various specific embodiments, those skilled in the art will recognize that the invention can be practiced with modification within the spirit and scope of the claims.

What is claimed is:

1. A process for the removal of immune complexes from a patient, said process comprising placing active receptor and receptor complex fractions on a suitable solid support and contacting said active receptor and receptor complex fractions with a patient's plasma containing immune complexes whereby the active receptor and receptor complex fractions are capable of binding to the immune complexes, wherein the process further comprises preparing said active receptor and receptor complex fractions from cell lines using ultrasonication or chelation.

2. A process in accordance with claim 1 wherein the solid support comprises a cartridge housed in a container.

3. A process in accordance with claim 2 wherein the cartridge comprises a filter or a hollow fiber cartridge.

4. A process in accordance with claim 3 wherein the cartridge is a removable cartridge.

5. A process in accordance with claim 2 where in the cartridge has pores.

6. A process in accordance with claim 5 wherein the pores have a size in the range from about 0.2 milli-microns to about 200 milli-microns.

7. A process in accordance with claim 6 wherein the pores have a size of about 0.45 milli-microns to about 45 milli-microns.

8. A process in accordance with claim 2 wherein the cartridges number from one to about 100 and are removable from a cartridge containing vessel.

9. A process in accordance with claim 1 wherein said immune complexes are removable from said plasma.

10. A process in accordance with claim 1 wherein the patient is a human.

11. A process in accordance with claim 2 which, further comprises adding antigens onto the solid support in combination with active receptor or receptor complex fractions.

12. A process in accordance with claim 11 wherein said antigens comprise dsDNA, antinuclear antibody, bacterial toxins and viral proteins.

13. A process in accordance with claim 2 which, further comprises adding antibodies on the solid support in combination with active receptor or receptor complex fractions.

14. A process in accordance with claim 13 wherein said antibodies are antibodies against antigens selected from the group consisting of dsDNA, antinuclear antibody, bacterial toxin and viral protein.

15. A process in accordance with claim 1 wherein the ultrasonication comprises applying ultrasonication to the cell lines in an amount of time and at a frequency sufficient to prepare active cell receptor fractions.

16. A process in accordance with claim 1, wherein the process further comprises preparing said active receptor and receptor complex fractions from cell lines using ultrasonication.

17. A process in accordance with claim 1, wherein the process further comprises preparing said active receptor and receptor complex fractions from cell lines using chelation.

* * * * *